United States Patent [19]

Steffen

[11] Patent Number: 5,101,043
[45] Date of Patent: Mar. 31, 1992

[54] PROCESS FOR THE PREPARATION OF 3-CARBOXAMIDO-5-VINYL-2-PYRROLIDONE

[75] Inventor: Klaus-Dieter Steffen, Hennef, Fed. Rep. of Germany

[73] Assignee: Huels Aktiengesellschaft, Marl, Fed. Rep. of Germany

[21] Appl. No.: 679,278

[22] Filed: Apr. 2, 1991

[30] Foreign Application Priority Data

Apr. 3, 1990 [DE] Fed. Rep. of Germany ....... 4010709

[51] Int. Cl.$^5$ .......................................... C07D 207/277
[52] U.S. Cl. .................................................. 548/537
[58] Field of Search ......................................... 548/537

[56] References Cited

U.S. PATENT DOCUMENTS 4,178,463  12/1979  Gittos et al. ..................... 548/537 X
4,235,778  11/1980  Gittos et al. ..................... 548/537 X

FOREIGN PATENT DOCUMENTS 2902438  8/1979  Fed. Rep. of Germany .

*Primary Examiner*—Joseph Paul Brust
*Attorney, Agent, or Firm*—Felfe & Lynch

[57] ABSTRACT

The preparation of 3-carboxamido-5-vinyl-2-pyrrolidone from a 2-vinylcyclopropyl-1,1-dicarboxylic acid dialkyl ester and ammonia is improved with respect to yield and purity of the end product by addition of an alkali metal alcoholate and a polymerization inhibitor.

4 Claims, No Drawings

PROCESS FOR THE PREPARATION OF 3-CARBOXAMIDO-5-VINYL-2-PYRROLIDONE

FIELD OF THE INVENTION

This invention relates to a novel process for the preparation of 3-carboxamido-5-vinyl-2-pyrrolidone (CAVP) from a 2-vinylcyclopropyl-1,1-dicarboxylic acid (VCD) ester and ammonia. More particularly, a 2-vinylcyclopropyl-1,1-dicarboxylic acid dialkyl ester is used as the starting compound, and the reaction is performed after adding a polymerization inhibitor such as hydroquinone and a catalyst such as an alkali metal alcoholate, pursuant to the following reaction sequence:

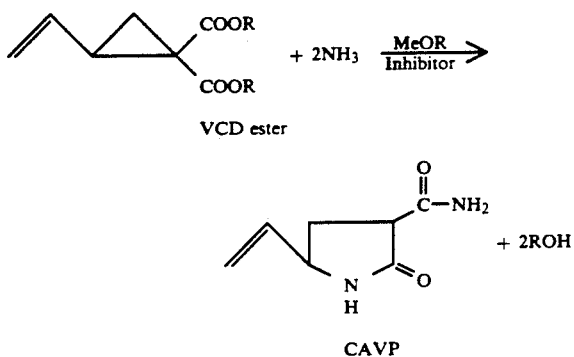

wherein Me is an alkali metal, and R is alkyl of 1 to 5 carbon atoms.

BACKGROUND OF THE INVENTION

The preparation and use of this pyrrolidone derivative is already described in German Offenlegungsschrift 29 02 438 (U.S. Pat. No. 4,178,463), but nothing is said about the yields and purity of the end product. The melting point of 215° C. mentioned in Example 3 of the above-mentioned published German application is an error, which is an indication that the synthesis of this substance pursuant to the process disclosed therein yields the end product with inferior purity (see Comparative Example below).

The pyrrolidone derivative is used for the preparation of 4-amino-hexene-5-acid, (4-vinyl-4-amino-butyric acid) which in turn is useful as an irreversible inhibitor of gamma-aminobutyric acid-transaminase.

The starting compound, 2-vinylcyclopropyl-1,1-dicarboxylic acid dialkyl ester of the formula:

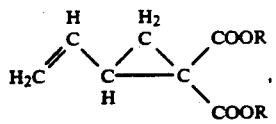

wherein R is alkyl of 1 to 5 carbon atoms, preferably methyl or ethyl, may be obtained in accordance with R. W. Kierstead et al, J. Chem. Soc. 1952, pages 3610 to 3616, from a malonic acid ester of the formula

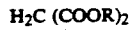

and trans-1,4-dibromobutene-2. The substituents R in the starting compound may be identical or different alkyls of 1 to 5 carbon atoms. This compound is always contaminated with 1,1dicarboxylic acid dialkyl ester cyclopentene-3, especially if the 1,4-dibromobutene-2 reactant is a mixture of the cis- and trans-isomers. Moreover, this vinylcyclopropyl compound tends to polymerize.

OBJECTS OF THE INVENTION

It is an object of the present invention to control the reaction in such a way that the 2-vinylcyclopropyl-1,1-dicarboxylic acid dialkyl ester can be used in the form of an impure raw product, and that the target product is nonetheless obtained with high purity and good yields.

Other objects and advantages of the invention will become apparent as the description thereof proceeds.

DESCRIPTION OF THE INVENTION

The above object is achieved in accordance with the present invention by performing the reaction after addition of a polymerization inhibitor, preferably hydroquinone, in amounts of 0.1 to 2.0 g, preferably 0.4 to 0.8 g, per mol of VCD ester, and of a catalyst such as an alkali metal alcoholate in amounts of 0.2 to 3%, preferably 0.5 to 1.5%, based on the amount of VCD ester. The alcoholate is advantageously used in the form of a solution in the corresponding alcohol of the VCD ester. The alcoholate is preferably an alkali metal alcoholate, especially sodium alcoholate or potassium alcoholate, or possibly also an alkaline earth metal alcoholate. It is thereby possible to use the VCD ester also as a raw product, that is, as an impure starting compound with purities of 50 to 98%. Side reactions and decompositions, for instance into ammonium carbonate, can be suppressed, so that the target product 3-carboxamido-5-vinyl-2-pyrrolidone (CAVP) is obtained with excellent purity of above 99% and good yields of about 65%. The yield of CAVP is based on the isomer mixture because the compound contains two asymmetric carbon atoms and is calculated on the basis of reacted VCD ester.

As a rule, the reaction is performed at 110° to 130° C. in 15 to 30 hours under a pressure of 10 to 15 bar. Lower alkanols, such as methanol or ethanol, are preferably used as solvents. The gaseous ammonia can be used in an excess of 1:3 (mols VCD ester: $NH_3$). At the conclusion of the reaction the ammonia excess is released into the solvent of a subsequent batch, so that only a little more than the stoichiometric amount of ammonia needs to be added to this subsequent reaction mixture.

The following Examples illustrate the present invention and will enable others skilled in the art to understand it more completely. It should be understood, however, that the invention is not limited solely to the particularly Examples given below.

COMPARATIVE EXAMPLE ANALOGOUS TO EXAMPLE 3 OF GERMAN OFFENLEGUNGSSCHRIFT 29 02 438

600 ml formamide and 112.5 g of raw 2-vinylcyclopropyl-1,1-dicarboxylic acid dimethyl ester (containing 81.7% pure VCD methyl ester, corresponding to 0.5 mol) were introduced into a 1-liter glass round-bottom flask, and the mixture was heated to 28° C. while stirring. After passing 270 g of ammonia gas therethrough over a period of 20 hours, the mixture was cooled and all of the formamide was distilled off in vacuo (16 to 2 mbar). The solid residue was recrystallized from about 200 ml of methanol. 26.1 g of 3-carboxamido-5-vinyl-2-pyrrolidone (33.8% of theory) having a melting point of 191° C. were obtained. By evaporation of the methanolic filtrate, an additional 6 g of highly contaminated target product were obtained.

EXAMPLE 1

112 g of raw 2-vinylcyclopropyl-1,1-dicarboxylic acid dimethyl ester (containing 82.4% pure VCD methyl ester, corresponding to 0.5 mol), 400 ml methanol, 0.2 g hydroquinone, and 1.12 g of sodium methylate as a methanolic solution (1% based on VCD methyl ester) were introduced in that order into a glass autoclave having a capacity of about 1.5 liters which was provided with a stirrer and was heated by means of an oil thermostat. After the autoclave was closed, 50 g of ammonia gas were introduced from a pressure cylinder, and the reaction was performed in 22 hours at 120° C. under a pressure of about 13 bar. After completion of the reaction the autoclave was cooled, the pressure was released, and the autoclave was emptied and rinsed out with methanol. The entire methanolic suspension was evaporated at standard pressure until crystallization set in, then cooled, and subsequently the 3-carboxamide-5-vinyl-2-pyrrolidone crystals which separated out were isolated and dried.

| | |
|---|---|
| Yield: | 49.9 g (64.7% of theory) |
| Melting point: | 191 to 193° C. |
| Purity (G.C.): | 99.5% |

EXAMPLE 2

137 g of raw 2-vinylcyclopropyl-1,1-dicarboxylic acid diethyl ester (containing 77.7% pure VCD ethyl ester, corresponding to 0.5 mol), 500 ml of ethanol, 0.5 g of hydroquinone, and 5 g of sodium ethylate in the form of a 20% ethanolic solution were introduced in that order into the same apparatus and under the same conditions as in Example 1, and then 52 g of ammonia gas were introduced under pressure. After 22 hours of reaction time at 123° C. and under a pressure of about 13 bar, the reaction mixture was cooled, the pressure was released, and the contents of the autoclave were emptied with ethanol into a glass round-bottom flask. The ethanol was distilled off until crystallization began, the mixture was cooled, and the crystallizate was filtered off, washed with ethanol and dried. The ethanolic filtrate was distilled whereby 29 g of unreacted VCD ethyl ester were recovered, which corresponds to a 73% conversion of the originally used VCD ethyl ester.

| | |
|---|---|
| Yield of CVAP: | 36 g (64.1% of theory) |
| Melting point: | 192 to 194° C. |
| Purity (G.C.): | 99.5% |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. In the method of preparing 3-carboxamido-5-vinyl-2-pyrrolidone by reacting a 2-vinylcyclopropyl-1,1-dicarboxylic acid dialkyl ester with ammonia at a temperature of 110° to 130° C., the improvement which comprises performing the reaction at a pressure of 10 to 15 bar in the presence of 0.1 to 2.0 g of hydroquinone per mol of 2-vinyl-cyclopropyl-1,1-dicarboxylic acid dialkyl ester and in the presence of 0.2 to 3.0% by weight of an alkali metal lower alkanolate, based on the weight of 2-vinylcyclopropyl-1,1-dicarboxylic acid dialkyl ester.

2. The method of claim 1, wherein the reaction is performed in the presence of 0.4 to 0.8 g of hydroquinone per mol of vinylcyclopropyldicarboxylic acid dialkyl ester.

3. The method of claim 1, wherein the reaction is performed in the presence of 0.5 to 1.5% by weight of an alkali metal lower alkanolate, based on the weight of vinylcyclopropyldicarboxylic acid dialkyl ester.

4. The method of claim 1, wherein a 2-vinylcyclopropyl-1,1-dicarboxylic acid alkyl ester with a purity of 50 to 98% is used as the starting material.

* * * * *